United States Patent
Ashby et al.

(10) Patent No.: US 6,964,658 B2
(45) Date of Patent: Nov. 15, 2005

(54) SYSTEM AND METHOD FOR FACILITATING HEMOSTASIS OF BLOOD VESSEL PUNCTURES WITH ABSORBABLE SPONGE

(75) Inventors: Mark Ashby, Laguna Niguel, CA (US); Luis R. Urquidi, Laguna Hills, CA (US); Eric Lee, Irvine, CA (US)

(73) Assignee: Sub-Q, Inc., Maple Grove, MN (US)

( * ) Notice: Subject to any disclaimer, the term of this patent is extended or adjusted under 35 U.S.C. 154(b) by 371 days.

(21) Appl. No.: 10/366,752

(22) Filed: Feb. 14, 2003

(65) Prior Publication Data

US 2003/0120258 A1 Jun. 26, 2003

Related U.S. Application Data

(63) Continuation of application No. 09/570,857, filed on May 12, 2000, now Pat. No. 6,540,735.

(51) Int. Cl.[7] .............................................. A61M 25/00
(52) U.S. Cl. .................... 604/523; 604/264; 604/15; 604/60; 604/537; 604/32; 604/33; 606/108; 606/191; 606/192
(58) Field of Search .................................. 604/523, 264, 604/11, 12, 13, 14, 15, 16, 17, 18, 57, 58, 59, 60, 93.01, 537, 286, 246, 247, 32, 33; 606/213, 108, 191, 192, 193, 194

(56) References Cited

U.S. PATENT DOCUMENTS

| 581,235 A | 4/1897 | Kenyon |
|---|---|---|
| 1,578,517 A | 3/1926 | Hein |
| 2,086,580 A | 7/1937 | Shirley |
| 2,370,319 A | 2/1945 | Lippincott |
| 2,465,357 A | 3/1949 | Correll |
| 2,492,458 A | 12/1949 | Bering, Jr. |

(Continued)

FOREIGN PATENT DOCUMENTS

| EP | 32826 A2 | 7/1981 |
|---|---|---|
| EP | 476178 A1 | 3/1992 |
| EP | 482350 A2 | 4/1992 |
| EP | 0557963 | 2/1993 |
| EP | 0637431 | 11/1994 |
| FR | 2 641 692 | 7/1990 |
| GB | 1509023 | 4/1978 |
| GB | 1569660 | 6/1980 |
| RU | 782814 | 11/1980 |
| RU | 1088709 A | 4/1984 |
| WO | WO 91/12847 | 9/1991 |
| WO | WO 94/02072 | 2/1994 |
| WO | WO 94/28800 | 12/1994 |

(Continued)

OTHER PUBLICATIONS

Berman, et al "Guided Direct Antegrade Puncture of the Superficial Femoral Artery" AJR 147:632–634, Sep. 1986 0361–803X/86/1473–0632 © American Roentgen Ray Society.

(Continued)

Primary Examiner—Henry Bennett
Assistant Examiner—Fadi H. Dahbour
(74) Attorney, Agent, or Firm—Miller, Matthias & Hull

(57) ABSTRACT

A system for facilitating hemostasis of a puncture site in a blood vessel delivers an absorbable sponge pledget in a hydrated state to a position at an exterior of the blood vessel puncture to facilitate hemostasis. The system includes a staging chamber, a delivery cannula, and a pusher. The staging chamber is used for hydrating a pledget of absorbable sponge, compressing the pledget, and delivering the pledget to the delivery cannula. The staging chamber may include a valve for facilitating hydration and staging of the pledget. The delivery cannula and pusher are used to accurately place the sponge pledget outside the blood vessel. An easy loader connector may be used to facilitate loading the dry pledget into the staging chamber.

6 Claims, 15 Drawing Sheets

U.S. PATENT DOCUMENTS

| | | |
|---|---|---|
| 2,507,244 A | 5/1950 | Correll |
| 2,558,395 A | 6/1951 | Studer |
| 2,597,011 A | 5/1952 | MacMasters, et al. |
| 2,680,442 A | 6/1954 | Linzmayer |
| 2,761,446 A | 9/1956 | Reed |
| 2,814,294 A | 11/1957 | Figge |
| 2,824,092 A | 2/1958 | Thompson |
| 2,874,776 A | 2/1959 | Hooe |
| 2,899,362 A | 8/1959 | Sieger, Jr. et al. |
| 3,157,524 A | 11/1964 | Artandi |
| 3,358,689 A | 12/1967 | Higgins |
| 3,411,505 A | 11/1968 | Nobis |
| 3,724,465 A | 4/1973 | Duchane |
| 3,736,939 A | 6/1973 | Taylor |
| 4,000,741 A | 1/1977 | Binard et al. |
| 4,098,728 A | 7/1978 | Rosenblatt |
| 4,211,323 A | 7/1980 | Olsen |
| 4,218,155 A | 8/1980 | Weidner |
| 4,219,026 A | 8/1980 | Layton |
| 4,224,945 A | 9/1980 | Cohen |
| 4,238,480 A | 12/1980 | Sawyer |
| 4,292,972 A | 10/1981 | Pawelchak |
| 4,323,072 A | 4/1982 | Rosenbluth et al. |
| 4,340,066 A | 7/1982 | Shah |
| 4,390,018 A | 6/1983 | Zulowski |
| 4,404,970 A | 9/1983 | Sawyer |
| 4,405,314 A | 9/1983 | Copi |
| 4,515,637 A | 5/1985 | Cioca |
| 4,573,576 A | 3/1986 | Krol |
| 4,587,969 A | 5/1986 | Gillis |
| 4,588,395 A | 5/1986 | Lemelson |
| 4,619,261 A | 10/1986 | Guerriero |
| 4,619,913 A | 10/1986 | Luck et al. |
| 4,644,649 A | 2/1987 | Seaman et al. |
| 4,645,488 A | 2/1987 | Matukas |
| 4,699,616 A | 10/1987 | Norwak et al. |
| 4,708,718 A | 11/1987 | Daniels |
| 4,744,364 A | 5/1988 | Kensey |
| 4,790,819 A | 12/1988 | Li et al. |
| 4,829,994 A | 5/1989 | Kurth |
| 4,832,688 A | 5/1989 | Sagae et al. |
| 4,839,204 A | 6/1989 | Yoshino |
| 4,850,960 A | 7/1989 | Grayzel |
| 4,852,568 A | 8/1989 | Kensey |
| 4,869,143 A | 9/1989 | Merrick |
| 4,890,612 A | 1/1990 | Kensey |
| 4,900,303 A | 2/1990 | Lemelson |
| 4,929,246 A | 5/1990 | Sinofsky |
| 4,936,835 A | 6/1990 | Haaga |
| 4,950,234 A | 8/1990 | Fujioka et al. |
| 5,007,895 A | 4/1991 | Burnett |
| 5,021,059 A | 6/1991 | Kensey et al. |
| 5,049,138 A | 9/1991 | Chevalier et al. |
| 5,053,046 A | 10/1991 | Janese |
| 5,061,274 A | 10/1991 | Kensey |
| 5,080,655 A | 1/1992 | Haaga |
| 5,108,421 A | 4/1992 | Fowler |
| 5,129,889 A | 7/1992 | Hahn et al. |
| 5,163,904 A | 11/1992 | Lampropoulos et al. |
| 5,167,624 A | 12/1992 | Butler et al. |
| 5,192,290 A | 3/1993 | Hilgal |
| 5,192,300 A | 3/1993 | Fowler |
| 5,192,301 A | 3/1993 | Kamiya et al. |
| 5,195,988 A | 3/1993 | Haaga |
| 5,219,899 A | 6/1993 | Panster et al. |
| 5,220,926 A | 6/1993 | Jones |
| 5,221,259 A | 6/1993 | Weldon et al. |
| 5,232,453 A | 8/1993 | Plass et al. |
| 5,242,683 A | 9/1993 | Klaveness |
| 5,254,105 A | 10/1993 | Haaga |
| 5,275,616 A | 1/1994 | Fowler |
| 5,282,827 A | 2/1994 | Kensey et al. |
| 5,310,407 A | 5/1994 | Casale |
| 5,320,639 A | 6/1994 | Rudnick |
| 5,322,515 A | 6/1994 | Karas et al. |
| 5,325,857 A | 7/1994 | Nabai et al. |
| 5,334,216 A | 8/1994 | Vidal et al. |
| 5,342,388 A | 8/1994 | Toller |
| 5,350,399 A | 9/1994 | Erlebacher et al. |
| 5,352,211 A | 10/1994 | Merskelly |
| 5,366,480 A | 11/1994 | Corriveau et al. |
| 5,370,656 A | 12/1994 | Shevel |
| 5,383,896 A | 1/1995 | Gershony et al. |
| 5,383,899 A | 1/1995 | Hammerslag |
| 5,385,550 A | 1/1995 | Su et al. |
| 5,388,588 A | 2/1995 | Nabai et al. |
| 5,391,183 A | 2/1995 | Janze et al. |
| 5,399,361 A | 3/1995 | Song et al. |
| 5,417,699 A | 5/1995 | Klein |
| 5,419,765 A | 5/1995 | Weldon et al. |
| 5,431,639 A | 7/1995 | Shaw |
| 5,437,292 A | 8/1995 | Kipshidze |
| 5,437,631 A | 8/1995 | Janzen |
| 5,443,481 A | 8/1995 | Lee |
| 5,447,502 A | 9/1995 | Haaga |
| 5,458,570 A | 10/1995 | May, Jr. |
| 5,467,780 A | 11/1995 | Nabai et al. |
| 5,478,352 A | 12/1995 | Folwer |
| 5,479,936 A | 1/1996 | Nabai et al. |
| 5,486,195 A | 1/1996 | Myers et al. |
| 5,490,736 A | 2/1996 | Haber |
| 5,507,279 A | 4/1996 | Fortune |
| 5,522,840 A | 6/1996 | Krajicek |
| 5,522,850 A | 6/1996 | Yomtov et al. |
| 5,526,822 A | 6/1996 | Burbank et al. |
| 5,527,332 A | 6/1996 | Clement |
| 5,529,577 A | 6/1996 | Hammerslag |
| 5,540,715 A | 7/1996 | Katsaros et al. |
| 5,542,914 A | 8/1996 | Van Iten |
| 5,545,175 A | 8/1996 | Abidin et al. |
| 5,545,178 A | 8/1996 | Kensey et al. |
| 5,558,853 A | 9/1996 | Quay |
| 5,571,168 A | 11/1996 | Toro |
| 5,591,204 A | 1/1997 | Janzen et al. |
| 5,591,205 A | 1/1997 | Fowler |
| 5,601,601 A | 2/1997 | Tal et al. |
| 5,601,602 A | 2/1997 | Fowler |
| 5,601,603 A | 2/1997 | Illi |
| 5,620,461 A | 4/1997 | Muijs Van De Moer et al. |
| 5,645,566 A | 7/1997 | Brenneman et al. |
| 5,649,547 A | 7/1997 | Ritchart et al. |
| 5,653,730 A | 8/1997 | Hammerslag |
| 5,665,107 A | 9/1997 | Hammerslag |
| 5,674,346 A | 10/1997 | Kundel |
| 5,676,689 A | 10/1997 | Kensey et al. |
| 5,681,279 A | 10/1997 | Roper et al. |
| 5,707,393 A | 1/1998 | Kensey et al. |
| 5,716,375 A | 2/1998 | Fowler |
| 5,725,498 A | 3/1998 | Janzen et al. |
| 5,741,223 A | 4/1998 | Janzen et al. |
| 5,769,086 A | 6/1998 | Ritchart et al. |
| 5,775,333 A | 7/1998 | Burbank et al. |
| 5,782,861 A | 7/1998 | Cragg et al. |
| 5,800,389 A | 9/1998 | Burney et al. |
| 5,810,806 A | 9/1998 | Ritchart et al. |
| 5,830,130 A | 11/1998 | Janzen et al. |
| 5,858,008 A | 1/1999 | Capaccio |
| 5,868,762 A | 2/1999 | Cragg et al. |
| 5,902,310 A | 5/1999 | Foerster et al. |
| 5,931,165 A | 8/1999 | Reich et al. |
| 5,948,425 A * | 9/1999 | Janzen et al. ................ 606/213 |

| | | | |
|---|---|---|---|
| 5,964,785 A | * 10/1999 | Desecki et al. | 604/523 |
| 5,984,950 A | 11/1999 | Cragg et al. | |
| 6,007,563 A | 12/1999 | Nash et al. | |
| 6,027,471 A | 2/2000 | Fallon et al. | |
| 6,027,482 A | 2/2000 | Imbert | |
| 6,033,427 A | 3/2000 | Lee | |
| 6,045,569 A | * 4/2000 | Kensey et al. | 606/213 |
| 6,048,357 A | * 4/2000 | Kontos | 606/213 |
| 6,056,768 A | 5/2000 | Cates et al. | |
| 6,066,325 A | 5/2000 | Wallace et al. | |
| 6,071,300 A | 6/2000 | Brenneman et al. | |
| 6,071,301 A | 6/2000 | Cragg et al. | |
| 6,086,607 A | 7/2000 | Cragg et al. | |
| 6,090,130 A | * 7/2000 | Nash et al. | 606/213 |
| 6,126,675 A | * 10/2000 | Shchervinsky et al. | 606/213 |
| 6,161,034 A | 12/2000 | Burbank et al. | |
| 6,162,192 A | 12/2000 | Cragg et al. | |
| 6,183,497 B1 | 2/2001 | Sing et al. | |
| 6,200,328 B1 | 3/2001 | Cragg et al. | |
| 6,315,753 B1 | 11/2001 | Cragg et al. | |
| 6,325,789 B1 | * 12/2001 | Janzen et al. | 604/15 |
| 6,350,274 B1 | * 2/2002 | Li | 606/213 |
| 6,371,974 B1 | 4/2002 | Brenneman et al. | |
| 6,440,151 B1 | 8/2002 | Cragg et al. | |
| 6,440,153 B2 | 8/2002 | Cragg et al. | |
| 6,447,534 B2 | 9/2002 | Cragg et al. | |
| 6,527,734 B2 | 3/2003 | Cragg et al. | |
| 6,540,735 B1 | 4/2003 | Ashby et al. | |
| 6,544,236 B1 | 4/2003 | Cragg et al. | |
| 6,610,026 B2 | 8/2003 | Cragg et al. | |
| 2002/0042378 A1 | 4/2002 | Reich et al. | |
| 2003/0088271 A1 | 5/2003 | Cragg et al. | |

FOREIGN PATENT DOCUMENTS

| | | |
|---|---|---|
| WO | WO 95/28124 | 10/1995 |
| WO | WO 95/32669 | 12/1995 |
| WO | WO 95/32671 | 12/1995 |
| WO | WO 95/32679 | 12/1995 |
| WO | WO9608208 | 3/1996 |
| WO | WO 96/24290 | 8/1996 |
| WO | WO 97/09934 | 3/1997 |
| WO | WO9086346 | 2/1998 |
| WO | WO 99/66834 | 12/1999 |

OTHER PUBLICATIONS

Berman et al "Modification of the Cope Drainage Catheter to Facilitate Placement" AJR 146:169–170, Jan. 1986 0361–803X/86/1461–0169 © American Ray Society.

Saddekni, MD et al "Antegrade Catheterization of the Superficial Femoral Artery" Radiology 1985 157:561–532.

Vogelzang "A Modified Cope Introducing Dilator to Allow Straight Guide Wire Introduction" AJR 146:381–382 Feb. 1986 0361–803X/86/1462–0381 © American Roentgen Ray Society.

Vincent P. Chuang, MD, et al. "Sheath Needle for Living Biopsy in High–Risk Patients," Radiology, vol. 166 (1988_ pp. 261–262.

Marc Zins, MD, et al., "US–guided Percutaneous Liver Biopsy with Plugging of the Needle Track: A prospective Study in 72 High–Risk Patients, " Radiology, vol. 184 (1992) p. 841–843.

Tony P. Smith, MD, et al. "Percutaneous Transhepatic Live Biopsy with Track Embolization," Radiology, vol. 198 (1996), pp. 769–774.

S.A. Riley, et al. "Precutaneous Liver Biopsy with Plugging of Needle Track: A Safe Method for Use In Patients with Impaired Coagulation", The Lancet (1964), p. 436.

David J. Allison, MD, et al., "Percutaneous Liver Biopsy and Track Embolization with Steel Coils," Radiology, vol 169 (1998), pp. 261–263.

Sigmund Silber, MD, FACC, "Rapid Hemostasis of Arterial Puncture Sites with Collagen in Patients Undergoing Diagnostic and Interventional Cardiac Cathererization," Clincial Cardiology, vol. 20 (1997), pp. 981–992.

Ferdinand Kiemeneij, MD, et al., "Improved Anticoagulation Management after Palmaz Schatz coronary Stent Implanatation by Sealing the Arterial Puncture Site with a Vascular Hemostasis Device", Catheterization and Cardiovascular Diagnosis, 30:317–322 (1993).

J.P.M. Foran, et al., "Early Mobilisation after Percutaneous Cardiac Catherisation Using Collagen Plug (VasoSeal) Haemostasis", Br Heart, vol. 69 (1993) pp. 424–429.

Schrader, R., "Collagen Application, "Cathertrizaion and Cardiovascular Diagnosis, (1992) pp. 298–302.

JSR Gibbs, "Fermoral Arterial Hemostasis, " Journal of Interventional Cardiology, V5 (1992) pp. 85–85.

W.G. Kussmaul, "Rapid Arterial Hemostasis," Journal of the American College of Cardiology, vol. 25 (1995) pp. 1685–1692.

Timothy A. Sanborn, MD, et al. "Multicenter Randomized Trail Comparing a Percutaneous Collagen Hemostasis Device wwith Conventional Manual Compression After Diagnostic Angiography and Angioplasty," Journal of American College of Cardiology, vol. 22 No. 5 (1993) pp. 1273–1279.

Pharmacia & Upjohn Manufacture Brochure "Gelfoam Sterile Sponge, Sterile Powder, and Sterile Film," (May 1997): pp. 1–34.

Pharmica & Upjohn Manufacture Brochure, "Gelfoam Sterile Powder, " (Feb. (1996).

Pharmacia & Upjohn Manufacture Brochure, "Gelfoam Sterile Powder, " (Mar. 1996).

Pharmacia & Upjohn Manufacture Specification "Gelfoam Sterile Sponge, Sterile Powder, and Sterile Film, " (Nov. 1996): pp. 1–23.

John T. Correll, et al., A new Physiologically absorbable sponge.

John T. Correll, et al. Biologic investigations of new absorbable sponge; p. 585.

Fandrich, C., et al. "Small guage gelfoam plug liver biopsy in high risk patients", Australian Radiology, vol. 40, pp. 230–234 (1996).

Journal of interventional cardiology vol. 5 No. 2 Jun.

Kassell, et al. Size of Intracanial aneurysm; vol. 12, No. 3, (1983).

Schievink, et al. The new england journal of medicaine; review articles; intracanial aneurysms; Jan. 2, 1997.

Szikora, et al. Combined Use of stents and cells to treat experimental wide–necked carotid aneuryms: Preliminary results; AJNR AM newradio1 15: 1091–1102, Jun. 1994.

Szikora, et al. Endovascular treatment of experimental anuerysms with liquid polymers: vol. 38, No. 2, Feb. 1996.

Turjman, et al. Combined stent implantation & endosacular coil placement for tretment of experimental wide–necked aneurysms:AJNRAM J. Neuroradio 15: 1087–1090 Jun. 1994.

Yoshimoto, et al cerebral anuerysms unrelated to arterial bifurcations; Acta neurochir (Wien) (96) 138: 958–964.

* cited by examiner

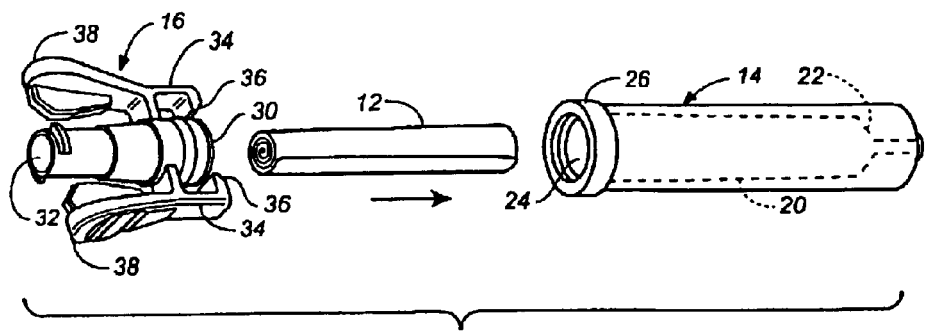
FIG._1
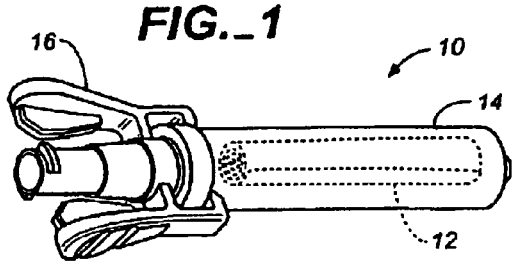
FIG._2
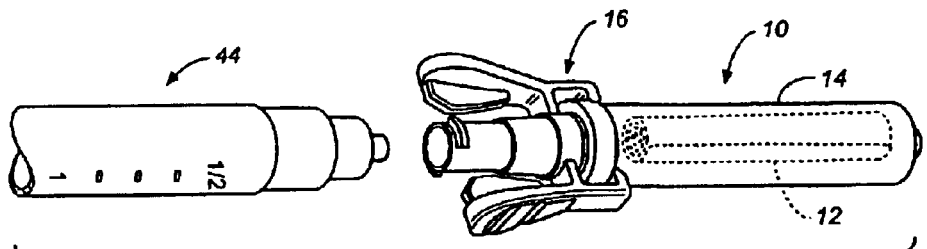
FIG._3
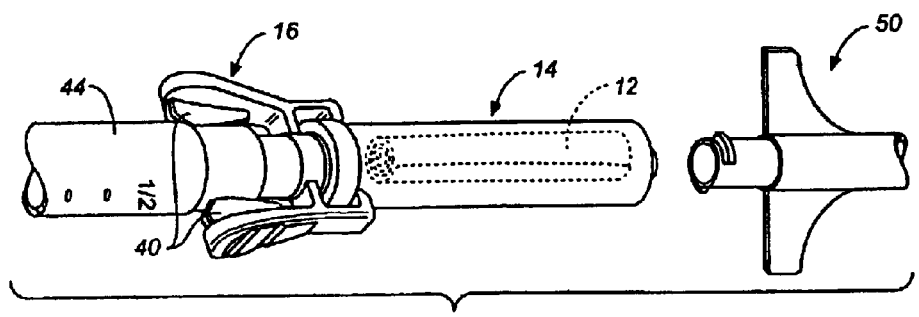
FIG._4

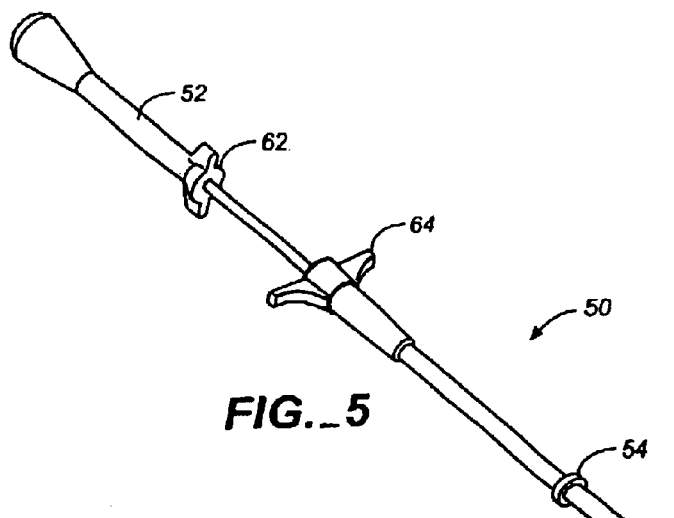
FIG._5
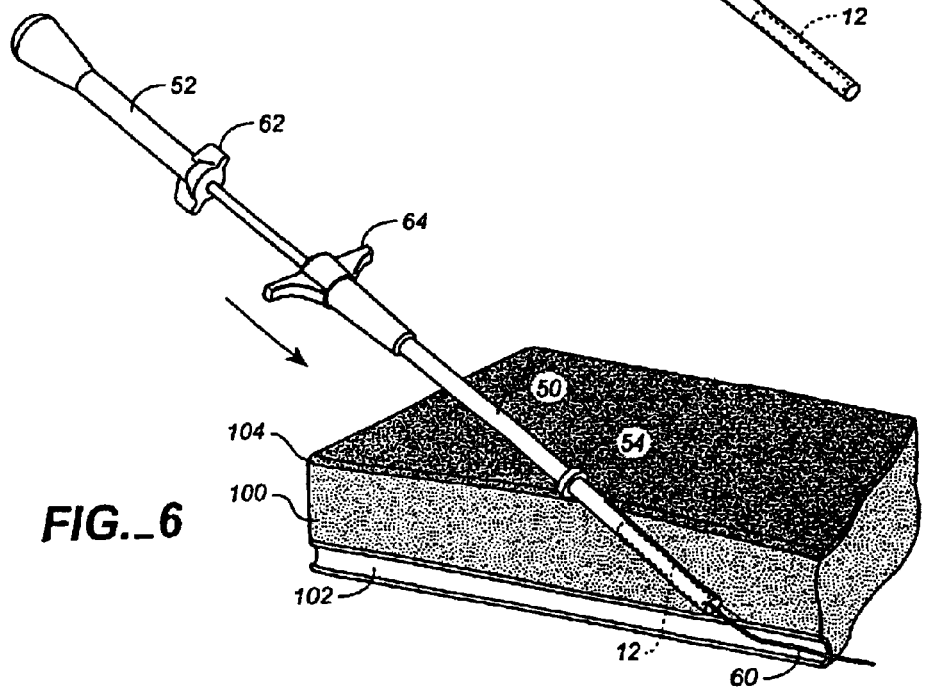
FIG._6

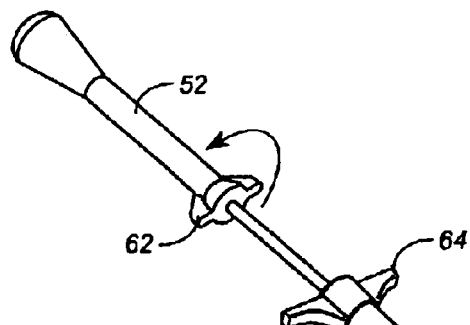
FIG._7
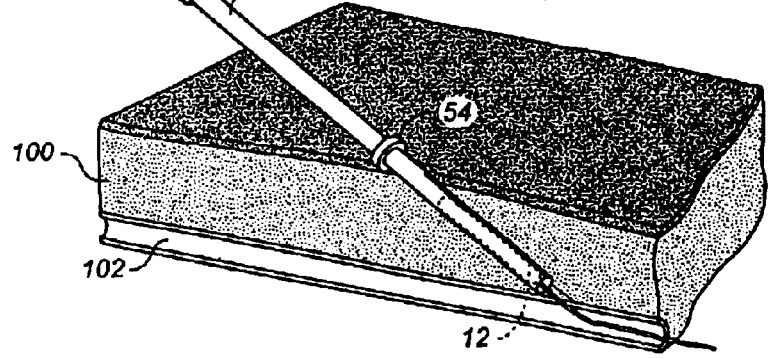
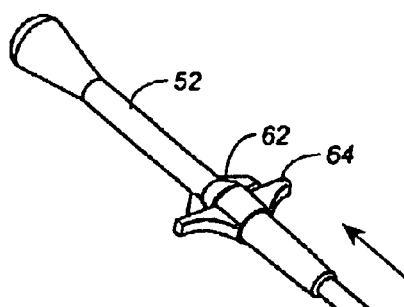
FIG._8
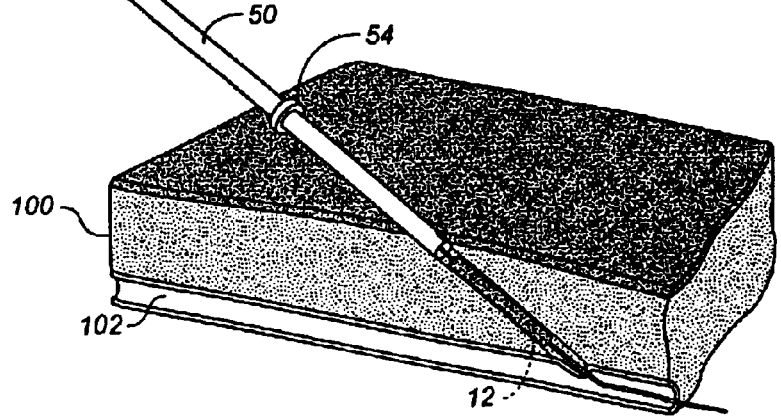

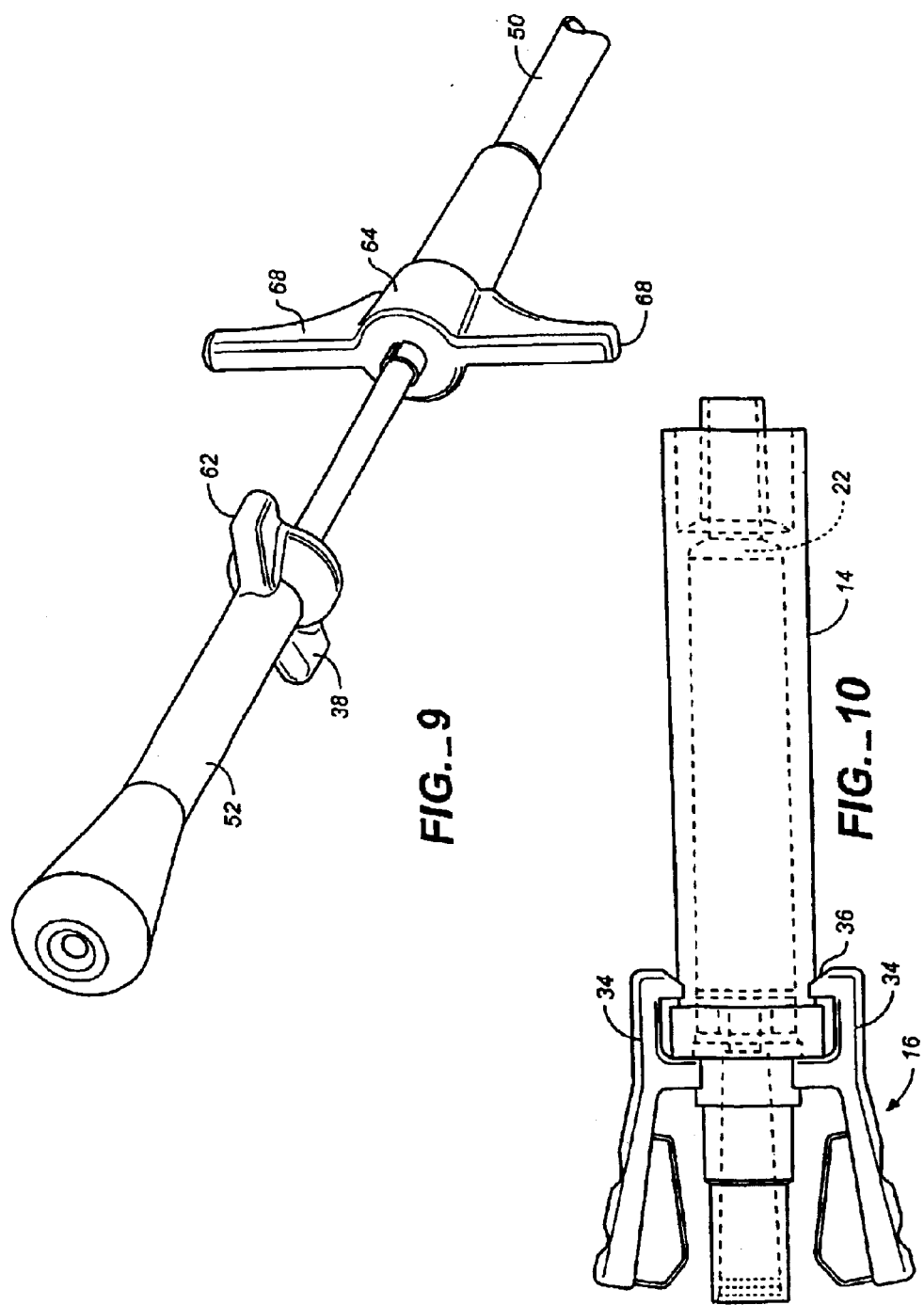

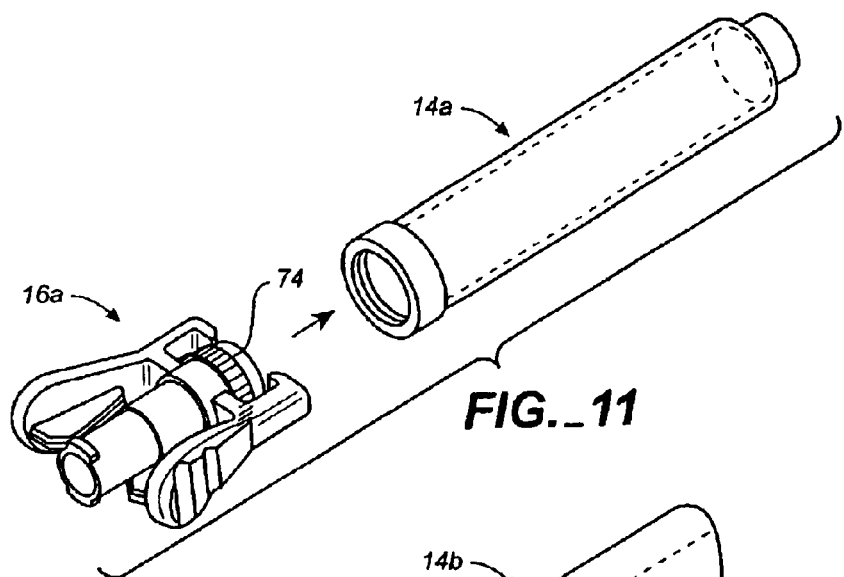
FIG._11
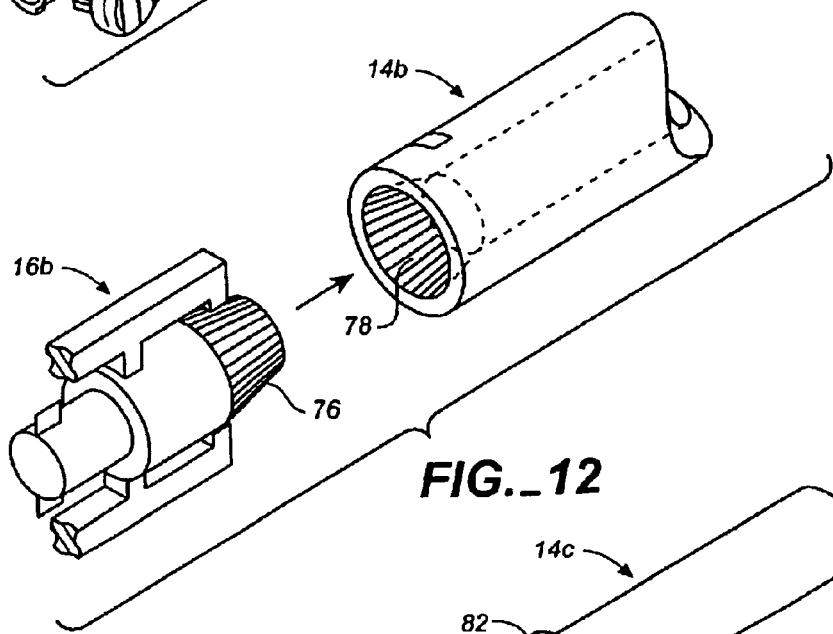
FIG._12
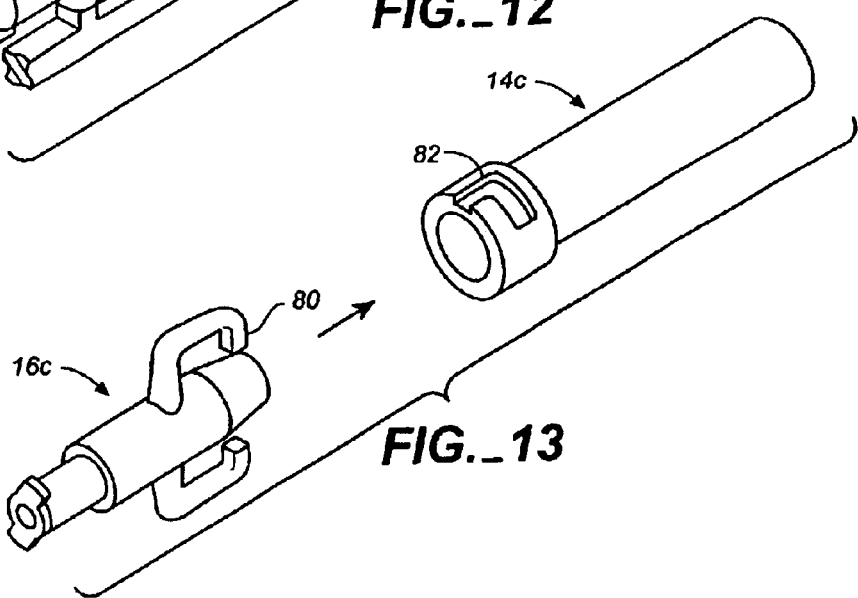
FIG._13

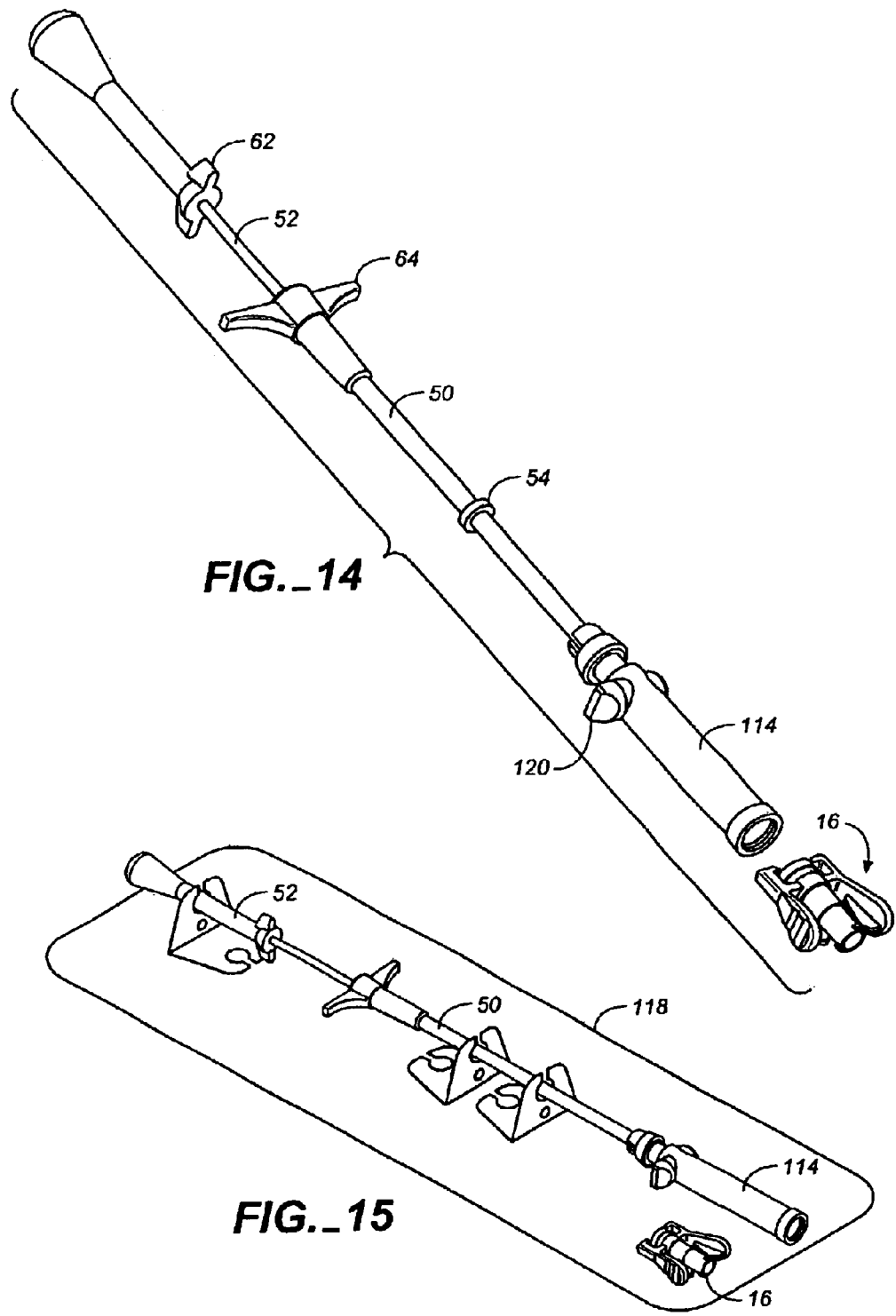
FIG._14
FIG._15

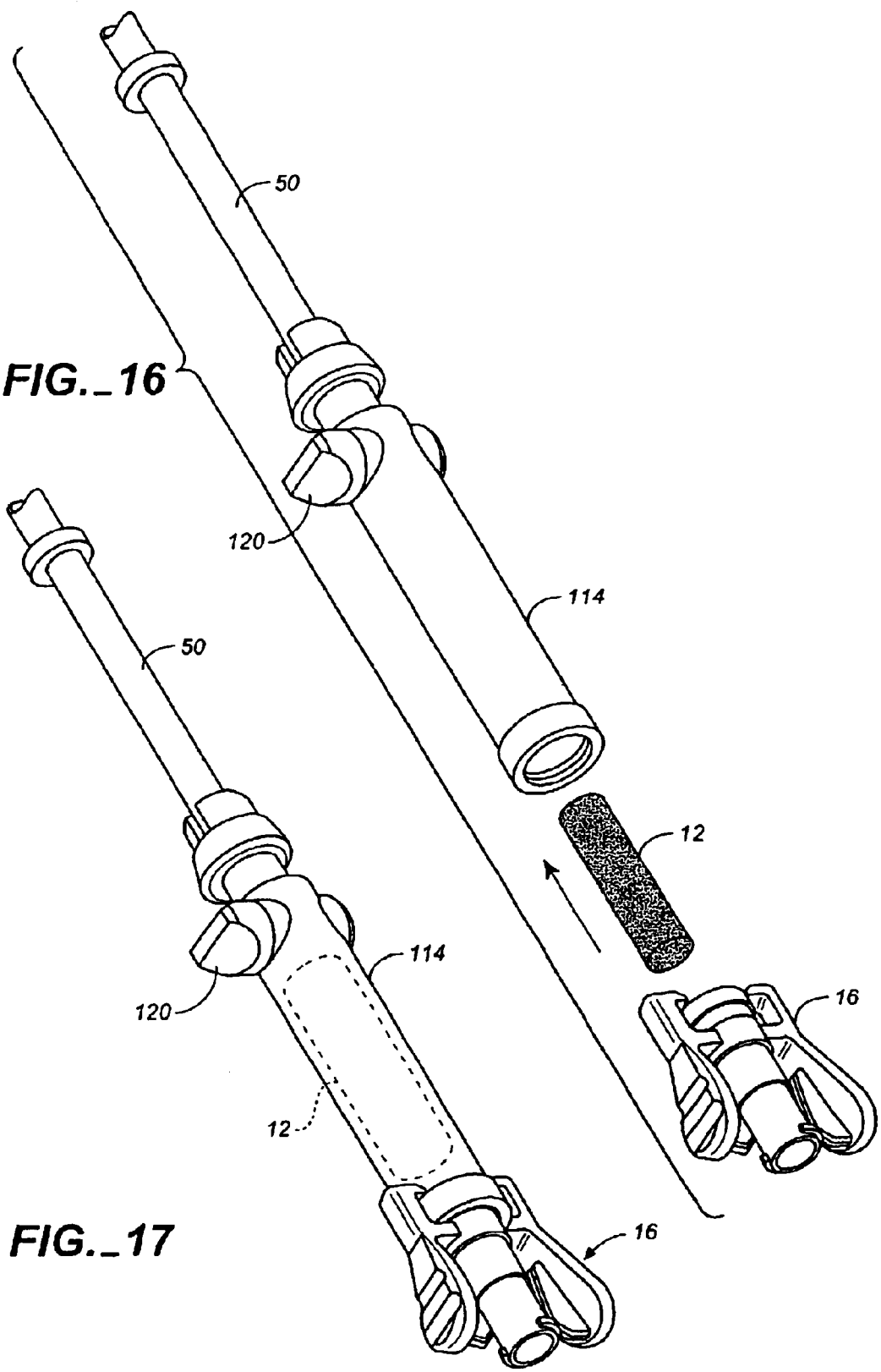

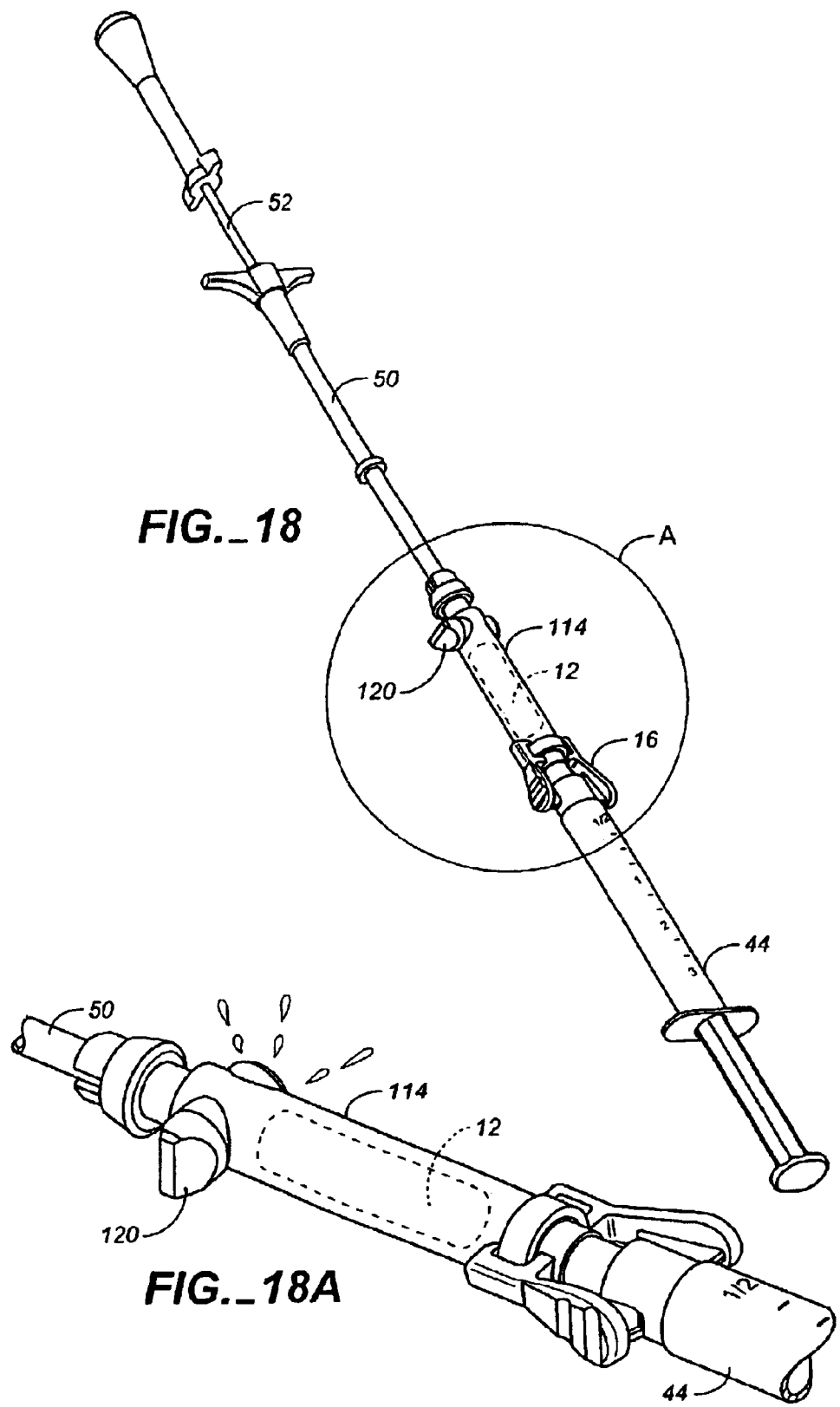
FIG._18
FIG._18A

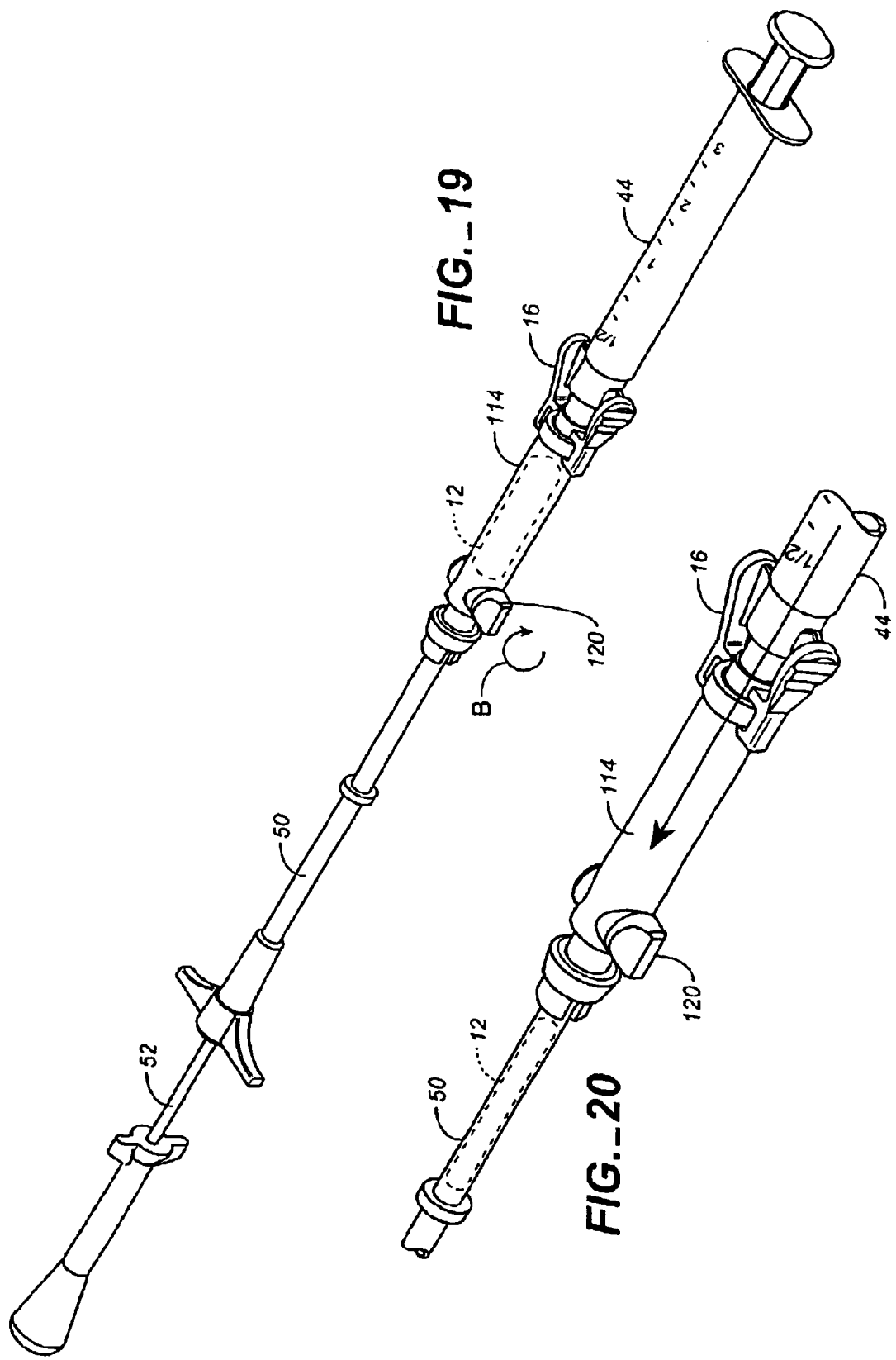

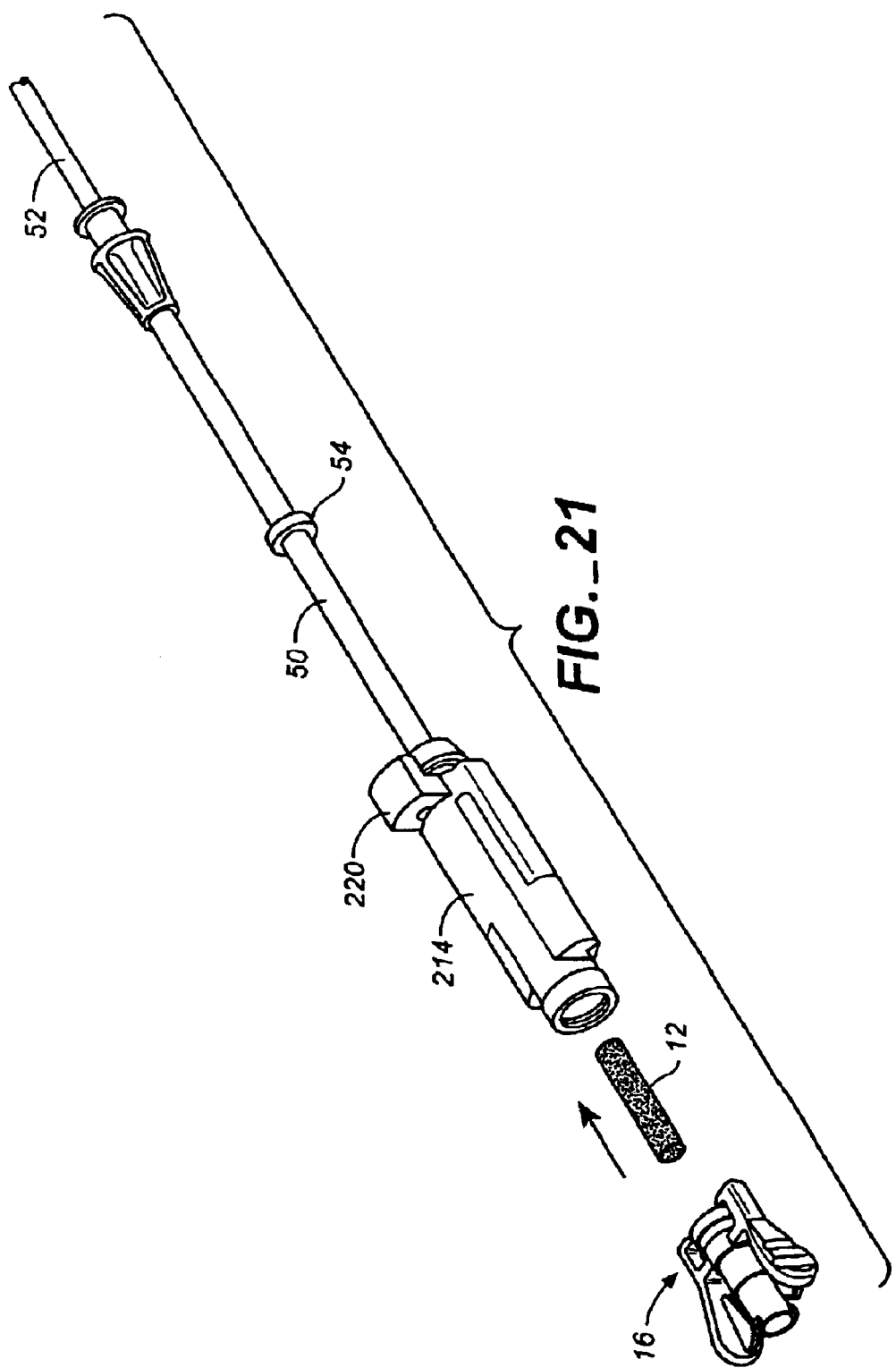
FIG._21

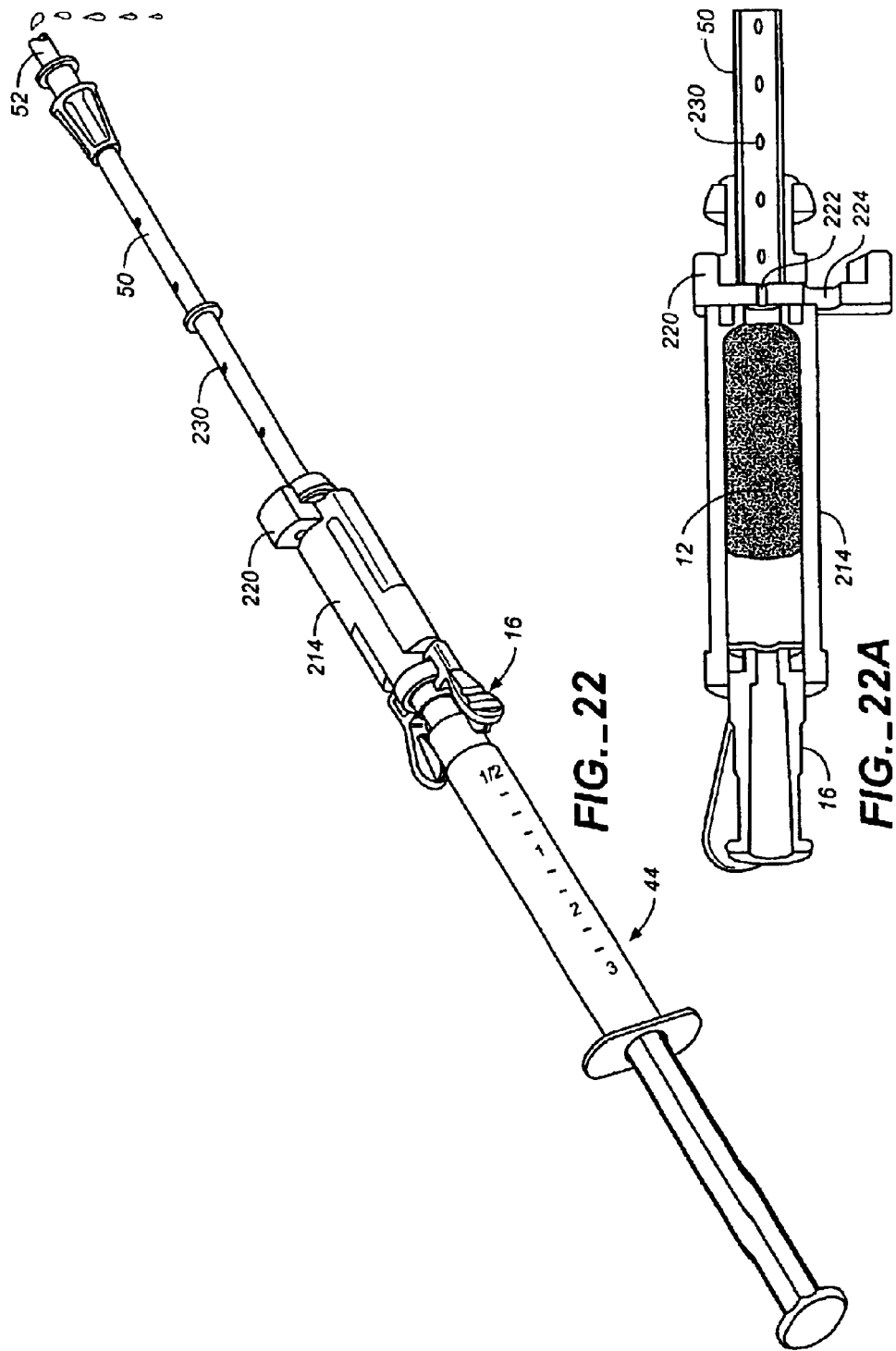

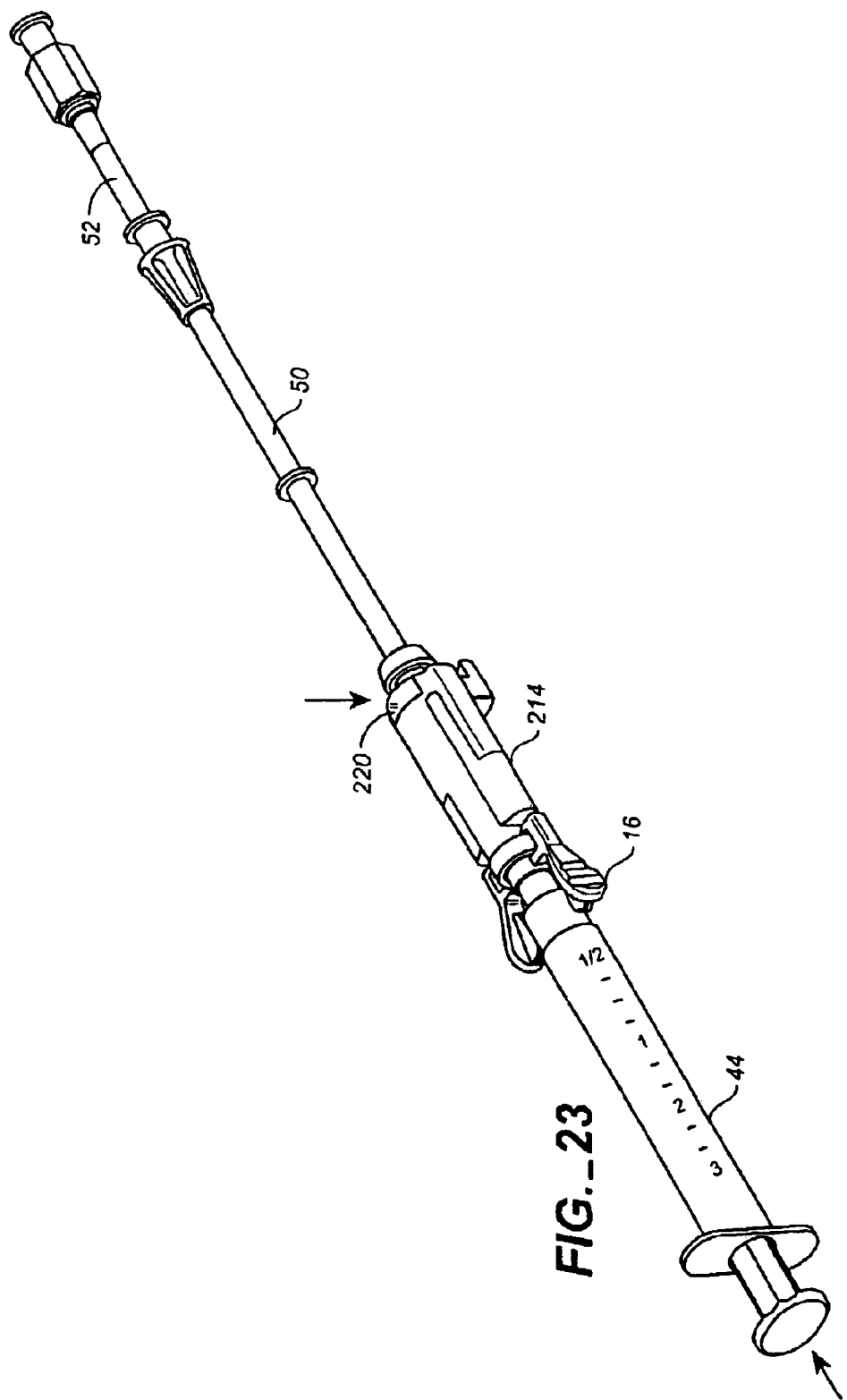

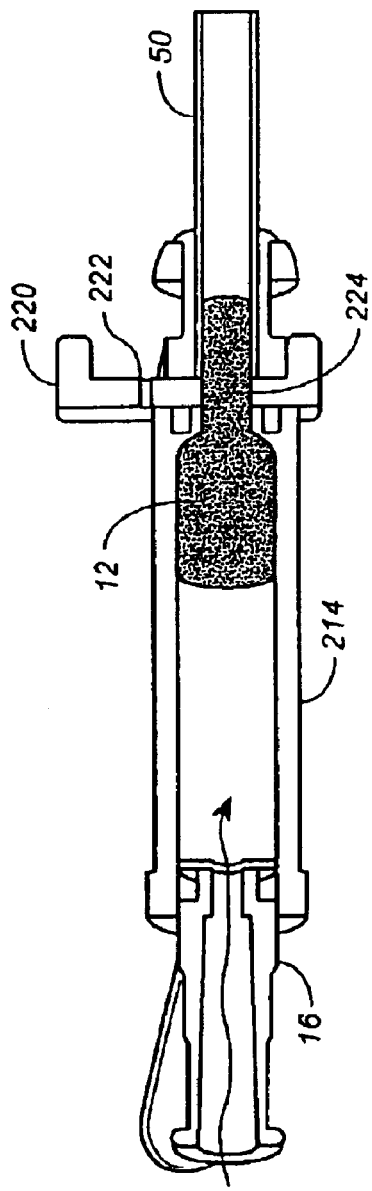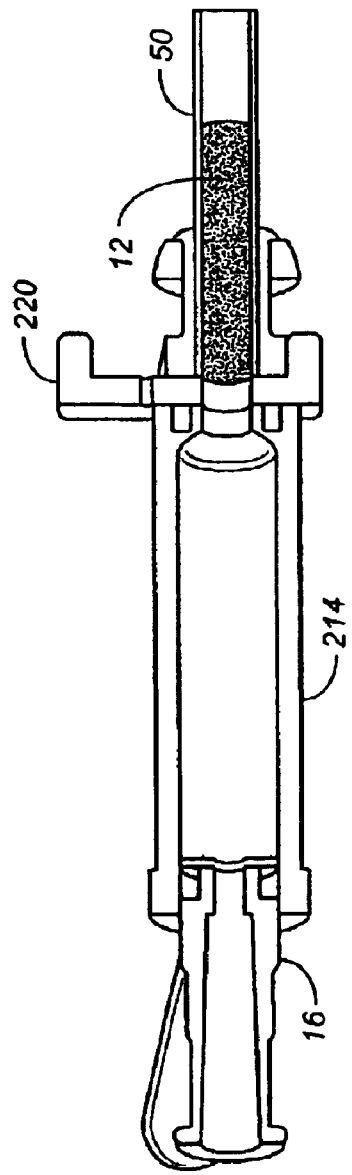

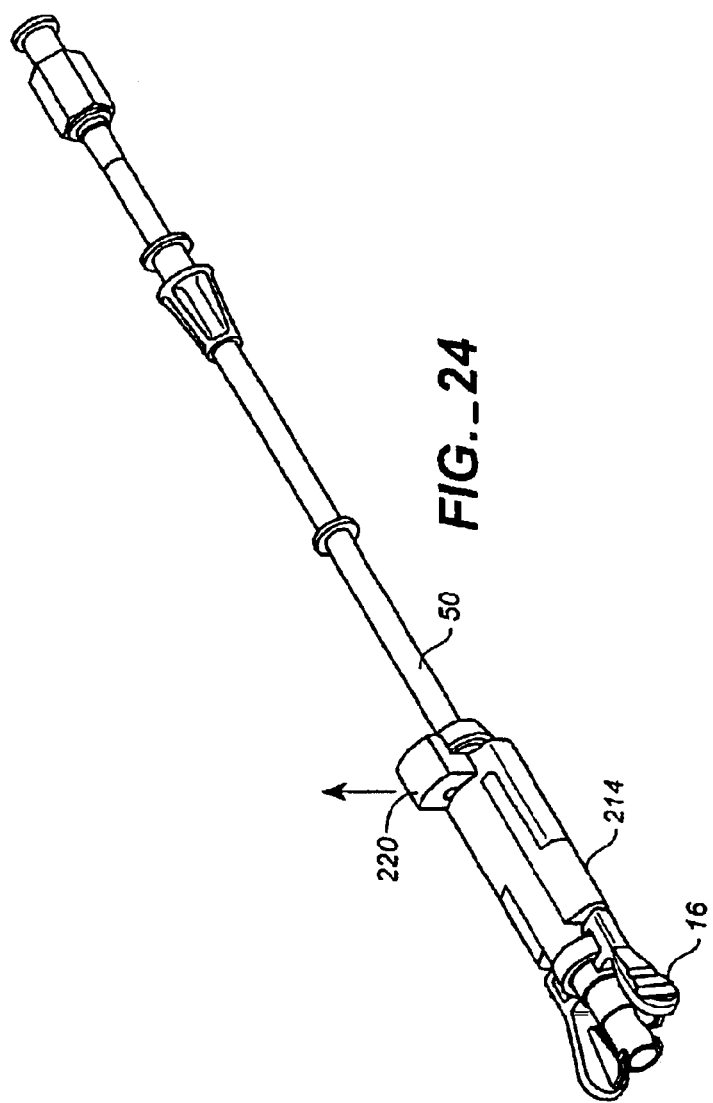
FIG._24
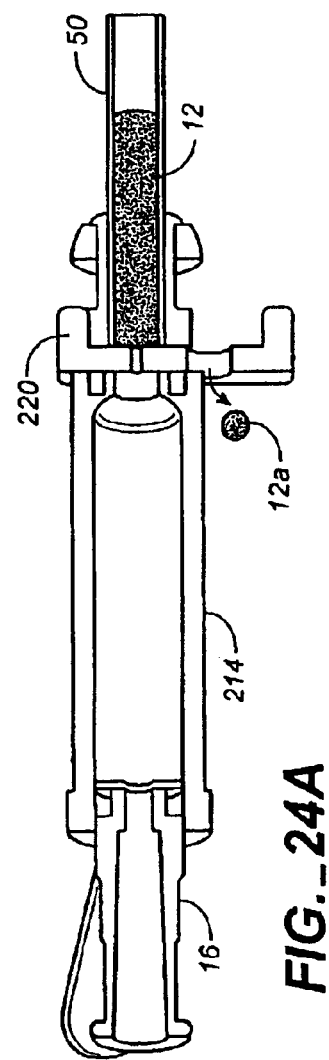
FIG._24A

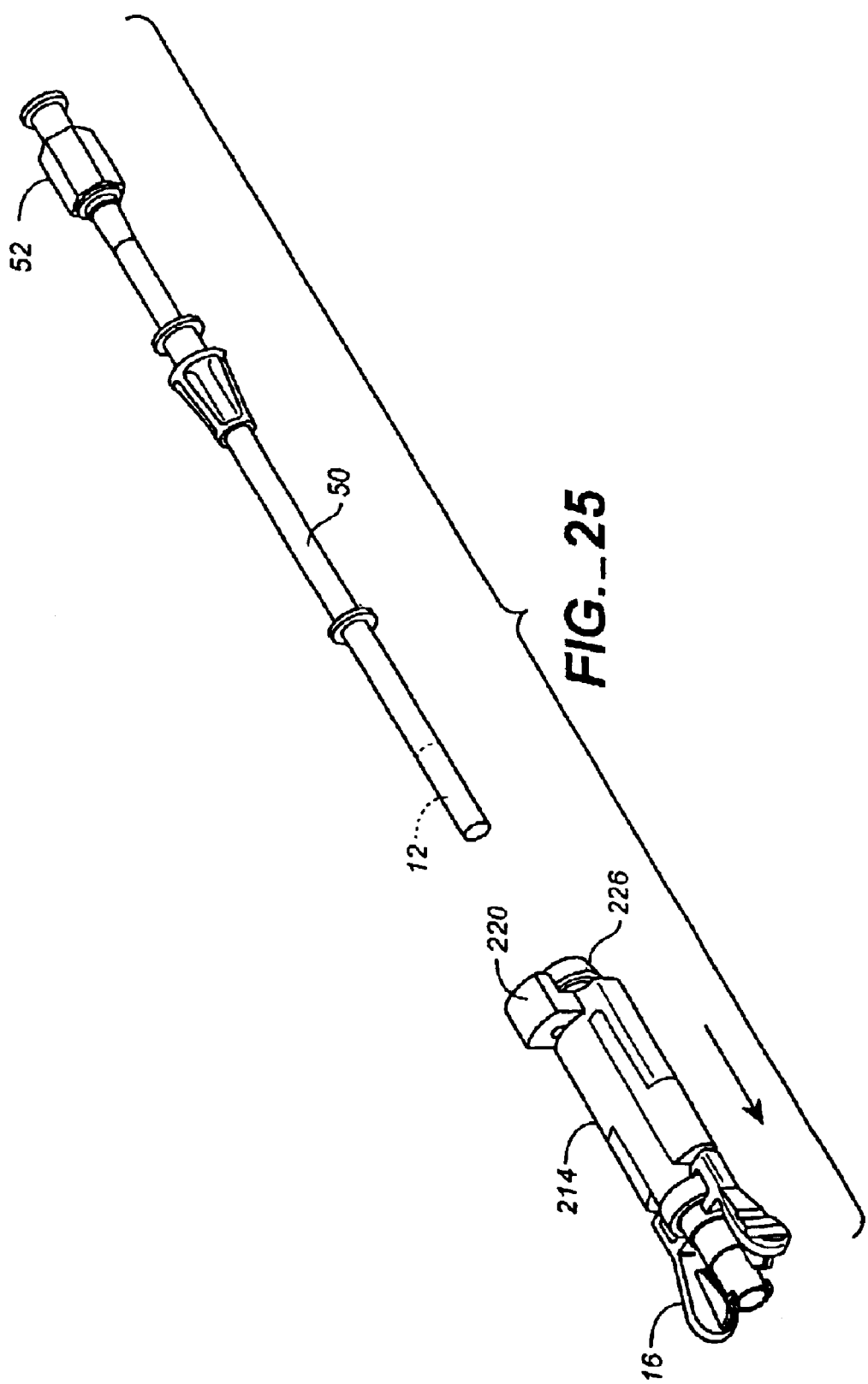
FIG._25

SYSTEM AND METHOD FOR FACILITATING HEMOSTASIS OF BLOOD VESSEL PUNCTURES WITH ABSORBABLE SPONGE

CROSS-REFERENCE TO RELATED APPLICATION

This application is a continuation of U.S. patent application Ser. No. 09/570,857, entitled "System and Method for Facilitating Hemostasis of Blood Vessel Punctures with Absorbable Sponge" by inventors Mark Ashby, Luis R. Urquidi and Eric Lee, filed on May 12, 2000 now U.S. Pat. No. 6,540,735.

BACKGROUND OF THE INVENTION

The invention relates to systems and devices for closure of blood vessel punctures, and more particularly, the invention relates to systems and methods for facilitating hemostasis of blood vessel punctures with an absorbable sponge material.

BRIEF DESCRIPTION OF THE RELATED ART

A large number of diagnostic and interventional procedures involve the percutaneous introduction of instrumentation into a vein or artery. For example, coronary angioplasty, angiography, atherectomy, stenting of arteries, and many other procedures often involve accessing the vasculature through a catheter placed in the femoral artery or other blood vessel. Once the procedure is completed and the catheter or other instrumentation is removed, bleeding from the punctured artery must be controlled.

Traditionally, external pressure is applied to the skin entry site to stem bleeding from a puncture wound in a blood vessel. Pressure is continued until hemostasis has occurred at the puncture site. In some instances, pressure must be applied for a up to an hour or more during which time the patient is uncomfortably immobilized. In addition, a risk of hematoma exists since bleeding from the vessel may continue beneath the skin until sufficient clotting effects hemostasis. Further, external pressure to close the vascular puncture site works best when the vessel is close to the skin surface and may be unsuitable for patients with substantial amounts of subcutaneous adipose tissue since the skin surface may be a considerable distance from the vascular puncture site.

More recently, devices have been proposed to promote hemostasis directly at a site of a vascular puncture. One class of such puncture sealing devices features an intraluminal anchor which is placed within the blood vessel and seals against an inside surface of the vessel puncture. The intraluminal plug may be used in combination with a sealing material positioned on the outside of the blood vessel, such as collagen. Sealing devices of this type are disclosed in U.S. Pat. Nos. 4,852,568; 4,890,612; 5,021,059; and 5,061,274.

Another approach to subcutaneous blood vessel puncture closure involves the delivery of non-absorbable tissue adhesives, such cyanoacrylate, to the perforation site. Such a system is disclosed in U.S. Pat. No. 5,383,899.

The application of an absorbable material such as collagen or a non-absorbable tissue adhesive at the puncture site has several drawbacks including: 1) possible injection of the material into the blood vessel causing thrombosis; 2) a lack of pressure directly on the blood vessel puncture which may allow blood to escape beneath the material plug into the surrounding tissue; and 3) the inability to accurately place the absorbable material plug directly over the puncture site.

The use of an anchor and plug system addresses these problems to some extent but provides other problems including: 1) complex and difficult application; 2) partial occlusion of the blood vessel by the anchor when placed properly; and 3) complete blockage of the blood vessel or a branch of the blood vessel by the anchor if placed improperly. Another problem with the anchor and plug system involves reaccess. Reaccess of a particular blood vessel site sealed with an anchor and plug system is not possible until the anchor has been completely absorbed because the anchor could be dislodged into the blood stream by an attempt to reaccess.

Yet another approach to subcutaneous puncture closure involves the internal suturing of the blood vessel puncture with a specially designed suturing device. However, these suturing devices involve a significant number of steps to perform suturing and require substantial expertise.

The use of a bioabsorbable hemostatic foam is a promising new alternative for promoting hemostasis of a blood vessel puncture site. One example of a hemostatic foam system for facilitating hemostasis of a puncture site is described in International Publication No. WO 99/56692 which is incorporated herein by reference in its entirety. As described in this application, a pledget of compressed hemostatic foam is cut from a sheet of the foam material and is rolled into a configuration which is inserted into a delivery device. Once the foam pledget is inserted into the delivery device, the foam is hydrated, compressed, and delivered to a body for promoting hemostasis of a blood vessel puncture site.

SUMMARY OF THE INVENTION

One aspect of the present invention relates to a device for facilitating hemostasis of a puncture in the wall of a blood vessel. The device includes a delivery chamber for delivery of a sponge pledget into a patient to seal a puncture, a pusher positioned in a proximal end of the introducer for ejection of the pledget from the delivery chamber into the patient to seal the puncture, and a staging chamber removably connectable to a distal end of the delivery chamber for hydrating the sponge pledget and delivering the sponge pledget to the delivery chamber, the staging chamber having a lumen diameter which is larger than a lumen diameter of the delivery chamber.

In accordance with another aspect of the present invention, a connector for introducing fluid to a chamber includes a connector body, a releaseable coupling for coupling a first end of the connector body to the opening of the chamber, a sealing mechanism for forming a substantially fluid tight seal between the first end of the connector body and the opening of the chamber, and a lock mechanism for preventing the release of the releaseable coupling when a syringe is connected to a second end of the connector body.

In accordance with an additional aspect of the present invention, a staging system for hydrating a sponge pledget includes a staging chamber having an open lumen with a tapered section at a first end, and a connector attachable to a second end of the staging chamber for connecting a syringe to the staging chamber. The connector includes a connector body having a central lumen, a first end for connection to the staging chamber, and a second end for connection to a syringe, a releasable coupling for coupling the first end of the connector body to the staging chamber, and a sealing mechanism for forming a substantially fluid tight seal between the first end of the connector and the staging chamber.

In accordance with a further aspect of the present invention, a device for facilitating hemostasis of a puncture in the wall of a blood vessel includes a delivery cannula for delivery of a sponge pledget into a patient to seal a puncture, a pusher positioned in a proximal end of the delivery cannula for ejection of the pledget from the delivery cannula into the patient to seal the puncture, and a staging chamber having a first end removably connectable to the delivery cannula. The staging chamber has a valve with a first position for hydrating the sponge pledget and a second position for delivering the sponge pledget to the delivery cannula. The staging chamber has a lumen diameter which is larger than a lumen diameter of the delivery cannula.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 1 is a perspective view of a staging system including a staging chamber, an easy loader connector, and a pledget;

FIG. 2 is a perspective view of the staging system of FIG. 1 with the pledget positioned in the staging chamber;

FIG. 3 is a perspective view of the staging system of FIG. 1 and a syringe for connection to the staging system;

FIG. 4 is a perspective view of the staging system of FIG. 1 which has been connected to a syringe for hydrating and delivering the pledget to a delivery chamber;

FIG. 5 is a perspective view of a pledget delivery system in which the pledget has been delivered to the delivery cannula by the staging system;

FIG. 6 is a perspective view of the delivery system of FIG. 5 delivered over a guidewire to a puncture site;

FIG. 7 is a perspective view of the delivery system of FIG. 5 in position for delivery of the pledget;

FIG. 8 is a perspective view of the delivery system of FIG. 5 with the pledget being delivered;

FIG. 9 is an enlarged perspective view of a portion of the delivery system of FIG. 5 showing the locking feature;

FIG. 10 is a side cross sectional view of the staging system of FIG. 1;

FIG. 11 is a perspective view of an alternative embodiment of the staging system;

FIG. 12 is a perspective view of a further alternative embodiment of the staging system;

FIG. 13 is a perspective view of an additional alternative embodiment of a staging system;

FIG. 14 is a perspective view of a front loader system for staging and delivering a pledget;

FIG. 15 is a perspective view of the front loader system of FIG. 14 mounted on a presentation card;

FIG. 16 is a perspective view of the front loader system of FIG. 14 during loading of a pledget into the staging chamber;

FIG. 17 is a perspective view of the front loader system of FIG. 14 with the pledget positioned in the staging chamber;

FIG. 18 is a perspective view of the front loader system of FIG. 14 with a syringe attached for hydrating and staging the pledget;

FIG. 18A is an enlarged perspective view of the portion A of FIG. 18;

FIG. 19 is a perspective view of the front loader system of FIG. 14 with a hydrated pledget;

FIG. 20 is a perspective view of the front loader system of FIG. 14 with the pledget loaded into a delivery cannula;

FIG. 21 is a perspective view of a front loader system including a staging chamber with a gate valve;

FIG. 22 is a perspective view of the front loader system of FIG. 21 with a syringe attached for hydrating and staging the pledget;

FIG. 22A is an enlarged cross section of a portion of FIG. 22;

FIG. 23 is a perspective view of the front loader system of FIG. 21 showing the pledget being delivered from the staging chamber to the delivery cannula;

FIG. 23A is a cross section of FIG. 23 while the pledget is being delivered to the delivery cannula;

FIG. 23B is a cross section of FIG. 23 when the pledget has been delivered into the delivery cannula;

FIG. 24 is a perspective view of the front loader system of FIG. 21 with the pledget delivered to the delivery cannula and any excess pledget material being removed;

FIG. 24A is an enlarged cross section of FIG. 24; and

FIG. 25 is a perspective view of the front loader system of FIG. 21 with the pledget positioned in the delivery cannula and the staging chamber removed.

DETAILED DESCRIPTION OF THE PREFERRED EMBODIMENTS

The absorbable sponge delivery systems described herein are used to deliver an absorbable sponge pledget in a hydrated condition to a blood vessel puncture site to achieve hemostasis. In general, the delivery systems include a staging chamber, a delivery cannula, and a pusher. The systems allow over the wire delivery of hydrated absorbable sponge material directly to the blood vessel puncture site to achieve hemostasis. Over the wire delivery ensures that the sponge material is properly positioned to fully occlude the puncture. In addition, the absorbable sponge material is delivered in a hydrated state which immediately expands to stop blood flow through the puncture. The staging chamber and delivery cannula allow the delivery of more absorbable sponge material through a smaller tract by hydrating and compressing the absorbable sponge material.

Prior to discussing the present invention in further detail, the following terms are defined:

"Pledget" means a piece of sponge formed into a generally elongated shape having a size which allows delivery in a hydrated state through a delivery cannula to a site of a puncture in a blood vessel.

"Sponge" means a biocompatible material which is capable of being hydrated and is resiliently compressible in a hydrated state. Preferably, the sponge is non-immunogenic and may be absorbable or non-absorbable.

"Absorbable sponge" means sponge which when implanted within a human or other mammalian body is absorbed by the body.

"Hydrate" means to partially or fully saturate with a fluid, such as, saline, water, contrast agent, thrombin, therapeutic agents, or the like.

"Kneading" of the absorbable sponge material means both dry and wet manipulation of sponge material which compresses, enlarges, or changes the shape of the sponge material causing the sponge material to have improved expansion response.

FIG. 1 illustrates a staging system 10 for hydrating and compressing an absorbable sponge pledget 12 and delivering the pledget into a delivery system. As discussed in further detail below, once the pledget 12 is positioned in the delivery system in a hydrated and compressed state, it is delivered over a guidewire to a blood vessel puncture site to promote hemostasis of the puncture. The staging system 10 includes a staging chamber 14 and an easy loader connector 16.

As shown in FIG. 1, the staging chamber 14 has an interior lumen 20 with a tapered portion 22 at a first end. A second end of the staging chamber 14 includes a loading opening 24 and an annular flange 26.

The easy loader connector 16 has a first end 30 for connection to the staging chamber 14 and a second end 32 including a luer fitting or other fitting for receiving a syringe or other fluid delivery member. The easy loader connector 16 also includes two snap fit tabs 34 with angled forward surfaces 36. The snap fit tabs 34 snap over the annular flange 26 on the staging chamber 14 to secure the easy loader connector 16 to the staging chamber. Each of the snap fit tabs 34 has a corresponding wing 38. The wings 38 are depressed inwardly to release the easy loader connector 16 from the staging chamber 14.

The easy loader connector 16 allows the loading opening 24 of the staging chamber 14 to be larger in diameter than the opening in a standard luer fitting which receives the syringe. The opening of a standard luer fitting is about 0.156 inches.

FIG. 10 is a side cross sectional view of the staging system 10 including the staging chamber 14 and the easy loader connector 16. FIG. 10 more clearly shows the tapered portion 22 of the staging chamber lumen for compressing the pledget 12 while the pledget is delivered to the delivery cannula 50. FIG. 10 also shows the angled forward surfaces 36 of the easy loader tabs 34 which provide an easy snap fit connection.

In use, the pledget 12 is inserted into the staging chamber 14 through the loading opening 24. The easy loader connector 16 is then attached to the staging chamber 14. A syringe 44, shown in FIG. 3, is attached to the easy loader connector to allow injection of fluid into the staging chamber to hydrate, advance, and compress the pledget 12. Preferably, a seal is provided between the easy loader connector 16 and the staging chamber 14. The seal will be described further below with respect to FIGS. 11-13.

FIG. 4 illustrates the staging system 10 connected to the syringe 44 in preparation for hydrating and staging the pledget 12. The pledget 12 may be hydrated by placing a finger or vent cap over the first end of the staging chamber 14 and rapidly injecting a hydrating fluid into the staging chamber 14 with the syringe. Alternatively, the pledget 12 can be hydrated after the staging system 10 is attached to the delivery cannula 50. The hydrated pledget is then injected into the delivery cannula 50 for delivery to the puncture site.

The easy loader connector 16 also includes a lock mechanism which prevents the connector from being disconnected from the staging chamber 14 when a syringe 44 is connected to the connector. The locking mechanism is provided by stops 40 on the wings 38. The stops 40 contact the side walls of the syringe 44 preventing the wings 38 from deflecting radially inward. This locking mechanism allows higher pressures to be used for hydration.

FIGS. 5–8 illustrate the steps of delivering a pledget 12 to a puncture site with a delivery system including the delivery cannula 50 and a pusher 52. The delivery cannula 50 includes a depth indicator 54 which is set in a manner such as is described in International Publication No. WO 99/56692.

The pusher 52 and delivery cannula 50 are provided with interengaging lock members 62, 64 which prevent or allow relative motion of the pusher and delivery cannula in one or two axial directions depending on the relative rotational position of the lock members. The lock member 64 on delivery cannula 50 also includes two wings which may be used as a handle.

FIG. 5 illustrates the delivery system with a pledget 12 loaded in a distal end of the delivery cannula 50 by using the staging chamber 14 as described above. One method of delivering an absorbable sponge pledget sponge 12 to facilitate hemostasis of a blood vessel puncture wound will now be described with respect to FIGS. 5–8.

After an intervascular procedure has been completed, a guidewire 60 is already in place passing through the subcutaneous tissue 100 and into the blood vessel 102. Alternatively, if a guidewire is not already in place the guidewire is inserted through an access sheath used in the intervascular procedure and the access sheath is then removed. The guidewire 60 is maintained in place with a proximal end extending from the patients body and a distal end extending through the skin 104 and subcutaneous tissue 100, and into the blood vessel 102. A proximal end of the guidewire 60 is fed into the distal end of the delivery cannula 50 through the hydrated and compressed pledget 12 and out a proximal end of the pusher 52.

Preferably, the guidewire 60 is fed through substantially the center of the pledget 12 to ensure that the implanted pledget is substantially centered over the blood vessel puncture. Alternatively, the guidewire may be inserted along a side of the pledget 12, through a separate second lumen of the delivery cannula 50, through an axial lumen in the pledget, or through a low density center of the pledget.

The delivery cannula 50 and pusher 52 are advanced together down through the skin 104 and subcutaneous tissue 100 until the depth indicator 54 on the exterior of the delivery cannula 50 is at the skin level. If a depth indicator is not used, the proper location of the cannula 50 is determined by palpation of the vessel with the cannula, by visualization, or by other means. According to a preferred embodiment, the lock members 62, 64 are in a locked position as shown in FIG. 6 during introduction of the delivery cannula 50 into the tissue to prevent relative motion of the cannula 50 and pusher 52 and thus, premature delivery of the pledget 12.

As shown in FIG. 7, the lock member 62 is rotated with respect to the lock member 64 to allow relative motion of the pusher 52 and delivery cannula 50 for delivery of the pledget. As shown in FIG. 8, the pusher 52 is held stationary while the delivery cannula 50 is withdrawn proximally preferably to a distance of about 75 percent of the length of the compressed, hydrated pledget 12. The 75 percent withdrawal distance may be indicated with appropriate markings on the delivery system. The portion of the pledget 12 which has been ejected into the tissue quickly expands upon delivery to fill the available space and provide localized compression. A slight forward pressure may then be maintained on the delivery cannula 50 and pusher 52 to increase local compression for a short period of time. The guidewire 60 is then removed and the delivery cannula 50 is withdrawn the remaining 25 percent. A slight forward pressure may be maintained again before the delivery cannula 50 and pusher 52 are removed from the patient. The delivered pledget 12 maintains hemostasis of the blood vessel puncture until healing occurs. The pledget 12 is preferably absorbed by the body over time.

FIG. 9 is an enlarged view of a portion of the delivery cannula 50 and the pusher 52 showing the lock members 62, 64. The lock members 62, 64 each include wings 38, 68 which, when aligned, allow the relative motion of the delivery cannula 50 and pusher 52. When the wings 38, 68 are unalligned, relative motion of the delivery cannula 50 and pusher 52 is prevented. Although a rotary lock has been shown the locking mechanism may be any of those known in the art.

FIGS. 11–13 illustrate alternative embodiments of the easy loader connector. As shown in FIG. 11, an easy loader connector 16a is provided with an O-ring or gasket seal 74 which provides a substantially fluid tight seal between the connector and the staging chamber 14a. The seal 74 may be any known seal, such as a silicone gasket. The seal 74 may conform to the shapes of the mating members for improved sealing.

FIG. 12 illustrates an alternative embodiment of the easy loader connector 16b in which a substantially fluid tight seal is provided by a conical beveled surface 76 on the connector and a correspondingly shaped beveled surface 78 on the opening of the staging chamber 14b.

FIG. 13 illustrates an alternative embodiment of a rotatable locking system or bayonet lock between an easy loader connector 16c and staging chamber 14c employing two locking fingers 80 and corresponding locking slots 82. A tapered sealing portion is also provided on the connector.

FIGS. 14–20 illustrate an alternative embodiment of a staging system in which a pledget is delivered into the delivery cannula 50 from a distal end of the delivery cannula. This system for delivering the pledget into the distal end of the delivery cannula 50 allows improved placement of the pledget in the delivery cannula because a distal end of the pusher 52 can be used as a stop to accurately locate the pledget. In addition, front loading delivery of the pledget into the delivery system reduces the number of steps for loading because the pusher can be located in the delivery cannula prior to the loading of the pledget.

The delivery system of FIG. 14 includes a delivery cannula 50, a pusher 52, a staging chamber 114, and an easy loader connector 16. As shown in FIG. 15, the delivery system of FIG. 14 can be provided in an assembled configuration in a kit and/or on a presentation card 118. The system of FIG. 15 is assembled and ready for loading of the pledget into the staging chamber 114.

FIGS. 16 and 17 illustrate the loading of the pledget into the staging chamber 114 and the connection of the easy loader connector 16 onto the staging chamber. A stopcock 120 is provided in the staging chamber 114 for venting a fluid during hydration of the pledget 12. As shown in FIGS. 18 and 118A, the syringe 44 is attached to the easy loader connector 16 and fluid is injected into the staging chamber 114 to hydrate the pledget 12. During hydration, excess fluid is vented through the stopcock 120 which is positioned in a venting position. After hydration, the stopcock 120 is rotated as illustrated by the arrow B in FIG. 19 to a delivery position for delivery of the pledget 12 from the staging chamber 114 into the delivery cannula 50 as illustrated in FIG. 20. Injection of fluid from the syringe 44 with the stopcock 120 in the delivery position delivers the pledget into the delivery cannula 50. The stopcock 120 may then be rotated to cut off or shear off a trailing portion the pledget 12. The staging chamber 114 is then removed from the delivery cannula 50 and the pledget is delivered to a puncture site in a blood vessel in the manner described with respect to the first embodiment.

FIGS. 21–25 illustrate an alternative embodiment of a staging chamber 214 including a sliding gate valve 220. The sliding gate valve may be used in place of the stopcock 120 of FIGS. 14–20. Although a rotating stopcock valve and a sliding gate valve have been illustrated, other types of valves may also be used.

FIG. 21 illustrates the loading of a pledget 12 into the staging chamber 214 which is connected to the delivery cannula 50. As shown in FIG. 22, after the pledget 12 is loaded into the staging chamber 214, the easy loader connector 16 and syringe 44 are connected to the staging chamber 214 for hydration of the pledget. As shown in FIG. 22A, the gate valve 220 is positioned in a first position such that a vent hole 222 is positioned between the staging chamber 214 and the delivery cannula 50. The vent hole 222 allows excess saline 230 injected into the staging chamber 214 to vent from the staging chamber into the delivery cannula 50.

After hydration of the pledget, the gate valve 220 is pushed to a second position, as shown in FIGS. 23 and 23A. In the second position a delivery opening 224 in the gate valve 220 is aligned with the staging chamber 214 to allow the pledget 12 to pass from the staging chamber into the delivery cannula 50.

In addition to providing for venting and delivery of the pledget 12, the gate valve 220 can be used as a guillotine or a cutter to cut or shear off portions of the pledget 12 which extend from the distal end of the delivery cannula 50. FIGS. 24 and 24A illustrate the sliding of the gate valve 220 from the second position for staging to the first position for venting to shear off the excess pledget material 12a adjacent the distal end of the delivery cannula. As shown in FIG. 25, a lock collar 226 is released to allow separation of the staging chamber 214 from the delivery cannula 50. The delivery cannula 50 and pusher 52 are then ready for over the wire insertion to a blood vessel puncture site to facilitate hemostasis.

One type of absorbable sponge material which is acceptable for use in the present invention is Gelfoam, manufactured by the Upjohn Company. Gelfoam is a porous, pliable, cross-linked gelatin material and is available commercially in sheet form as pre-compressed or non-compressed sponge. The material may be provided preformed as a pledget 12 or may be cut with a punch, or a stencil or template and knife and rolled to form a pledget as described above. Once hydrated, the pledget 12 can be easily compressed to fit into a lumen having a smaller cross sectional area than the original cross sectional area of the pledget. Additionally, the kneading of the hydrated pledget 12 during delivery encourages air trapped within the Gelfoam to be expelled and replaced with fluid, allowing rapid expansion upon delivery. When a pledget 12 of a pre-compressed Gelfoam is hydrated and kneaded (expelling air) during delivery, the pledget will have the absorption capacity to rapidly expand to many times (e.g., 3 or more times) its original dry volume upon delivery. When a pledget 12 of the non-compressed Gelfoam is hydrated and kneaded (expelling air) during delivery, the pledget will have the absorption capacity to rapidly expand to its original dry volume upon delivery. These properties make the Gelfoam sponge material particularly useful for facilitating hemostasis of puncture wounds by injection.

The absorbable sponge material can be absorbed by the body in a period of time between several days and several months depending on the absorbable sponge material used. A pledget 12 formed of commercially available Gelfoam material will be absorbed by the body within 1 to 6 weeks. However, the pledget material may be engineered to provide different rates of absorption. For example, Gelfoam can be designed to be absorbed at different rates by varying the degree of cross-linking. Preferably, the pledget 12 is designed to be absorbed in less than one month.

Although the invention is primarily intended for delivery of absorbable sponge, non-absorbable sponge may also be delivered with the devices, systems, and methods of the present invention. A non-absorbable sponge may be desirable where it will be necessary to locate the blood vessel puncture after the procedure.

Although the pledget 12 has been described as formed from a rectangular shaped piece of an absorbable sponge material which is rolled into a cylindrical shape, the pledget may also be formed in different shapes and rolled from different shaped sheets. For example, the pledget 12 may be preformed in a variety of cross sections including circular, rectangular, star, or other multi-sided shape. The pledget 12 may have a folded cross section and may have through or blind holes formed in the dry pledget. In addition, the pledget size and shape can be matched to the size and shape of a particular delivery site.

While an amorphous or discontinuous sponge structure may be used in the present invention, a continuous structure of the delivered absorbable sponge pledget 12 provides more secure and reliable placement of a plug of material against the blood vessel puncture than a paste or liquid. The continuous sponge structure can even facilitate partial withdrawal, removal, or movement of the ejected pledget.

In accordance with one aspect of the invention, the absorbable sponge material can be hydrated with a clotting agent such as thrombin, a contrast agent, another beneficial agent, a combination of agents, or the like. Alternatively, the pledget material itself may contain an agent such as a clotting agent, a contrast agent, another beneficial agent, a combination of agents, or the like.

The treatment of a blood vessel puncture with a hydrated and injected pledget 12 of absorbable sponge to facilitate hemostasis provides substantial advantages in comfort over external pressure methods. In addition, the present invention also provides advantages over the insertion of an absorbable sponge material in a dry state or injection of a liquid or paste. In particular, the hydration and manipulation or "kneading" of the hydrated Gelfoam pledget 12 as it is passed through the staging chamber improves the expansion and absorption characteristics of the Gelfoam. The injected Gelfoam conforms in shape quickly to the shape of the puncture site and immediately begins blocking blood flow through the puncture site and providing local compression. In contrast, a dry piece of sponge material does not swell until the blood has sufficiently saturated the sponge material, which can take up to hours. The hydrated and kneaded sponge material will expand to a larger size much more quickly when wetted than a piece of dry sponge material when wetted.

Because the amount of subcutaneous fat and tissue between the skin and the blood vessel varies between patients from approximately 0.5 cm to 15 cm or more the system may be provided in different lengths for use in different patients. The pledget 12 size and shape may also be varied for different patients. The absorbable sponge material should form a complete plug over the puncture site without expanding into the blood vessel or exiting the skin of the patient. In some instances where the amount of subcutaneous tissue is great it may be desirable to deliver multiple pledgets 12 in spaced apart positions along the tract leading to the puncture site. The particular size and shape of the delivery system may vary depending on the size of the access site, amount of subcutaneous tissue, and the size of pledget 12 to be delivered. While the invention has been described in detail with reference to the preferred embodiments thereof, it will be apparent to one skilled in the art that various changes and modifications can be made and equivalents employed, without departing from the present invention.

What is claimed is:

1. A device for facilitating hemostasis of a puncture in the wall of a blood vessel, comprising:
   a delivery sheath for delivery of a sponge pledget into a patient to seal a puncture; and
   a staging chamber having a first end removably connectable to the delivery sheath, the staging chamber having a valve with a first position for hydrating the sponge pledget and a second position for delivering the sponge pledget to the delivery sheath, the staging chamber having a lumen diameter which is larger than a lumen diameter of the delivery sheath.

2. The device of claim 1, wherein the valve is a rotatable stopcock.

3. The device of claim 1, wherein the valve is a gate valve.

4. The device of claim 1, wherein the valve includes a vent hole for venting fluid from the staging chamber when the vent is in the first position for hydrating.

5. The device of claim 1, wherein the valve includes a delivery opening for delivering the sponge pledget through the valve to the delivery cannula when the valve is in second position for deliver.

6. The device of claim 1, wherein the valve acts as a cutter when moved from the second position to the first position to cut off a portion of the sponge pledget.

* * * * *

UNITED STATES PATENT AND TRADEMARK OFFICE
CERTIFICATE OF CORRECTION

PATENT NO. : 6,964,658 B2  Page 1 of 1
APPLICATION NO. : 10/366752
DATED : November 15, 2005
INVENTOR(S) : Ashby et al.

It is certified that error appears in the above-identified patent and that said Letters Patent is hereby corrected as shown below:

1 col. Line 41
On page 3, under "Other Publications", please add:

--J. Bryne Review Article: *Endovascular Treatments for Intracranial Aneurysms*, The British Journal of Radiology, 1996, pages 98, 891-899--

Signed and Sealed this

Thirteenth Day of March, 2007

JON W. DUDAS
*Director of the United States Patent and Trademark Office*